(12) United States Patent
Kurschel (10) Patent No.: US 11,278,659 B2
(45) Date of Patent: Mar. 22, 2022

(54) ATTACHMENT FOR A DEVICE FOR GENERATING AN AIRFLOW

(71) Applicant: Earbreeze GmbH, Vienna (AT)

(72) Inventor: Martin Kurschel, Vienna (AT)

(73) Assignee: Earbreeze GmbH, Vienna (AT)

( * ) Notice: Subject to any disclaimer, the term of this patent is extended or adjusted under 35 U.S.C. 154(b) by 288 days.

(21) Appl. No.: 16/293,215

(22) Filed: Mar. 5, 2019

(65) Prior Publication Data
US 2020/0016004 A1    Jan. 16, 2020

(30) Foreign Application Priority Data
Jul. 13, 2018   (EP) ...................................... 18183454

(51) Int. Cl.
*A47K 10/48*   (2006.01)
*A45D 20/12*   (2006.01)
(Continued)

(52) U.S. Cl.
CPC ............. *A61M 3/0279* (2013.01); *A61F 7/12* (2013.01); *A61F 11/08* (2013.01); *A61F 2007/0005* (2013.01); *A61F 2007/0059* (2013.01); *A61F 2007/0069* (2013.01); *A61F 2007/0087* (2013.01); *A61F 2011/085* (2013.01); *A61M 2206/16* (2013.01); *A61M 2210/0662* (2013.01); *F26B 9/003* (2013.01)

(58) Field of Classification Search
CPC .................. A61F 7/12; A61F 2007/005; A61F 2007/0059; A61F 2007/0069; A61F 2007/0087; A61F 11/08; A61F 2011/085; A61F 11/006; A61M 3/0279; A61M 3/025; A61M 2206/16; A61M 2210/0662; A47K 10/48; A45D 20/00; A45D 20/12; A56D 20/12; F26B 9/003; A61B 1/227; A61B 1/2275
USPC ........................................................ 34/96–97
See application file for complete search history.

(56) References Cited

U.S. PATENT DOCUMENTS 5,364,343 A * 11/1994 Apolet ................ A61M 3/0283
                                                                                 239/124
6,210,358 B1 * 4/2001 Roger ..................... A61B 1/227
                                                                                 604/43
(Continued)

FOREIGN PATENT DOCUMENTS

CN         1295826 A    5/2001
CN       104797220 A    7/2015
(Continued)

OTHER PUBLICATIONS

International Search Report Application No. PCT/EP2019/068915 Completed: Sep. 6, 2019; dated Sep. 20, 2019 13 pages.
(Continued)

*Primary Examiner* — Camtu T Nguyen
(74) *Attorney, Agent, or Firm* — Whitmyer IP Group LLC (57) ABSTRACT

An attachment for a device for generating an airflow or for dispensing a fluid, which attachment is adapted to be inserted at least in sections into an external ear canal of a human or animal ear. The attachment has a connecting piece for connecting the attachment to the device for generating an airflow, and has a guide vane of tongue-like design with a guide vane base for guiding air flowing out of the device for generating an airflow via the connecting piece.

19 Claims, 7 Drawing Sheets

(51) Int. Cl.
*A61B 1/227* (2006.01)
*A61M 3/02* (2006.01)
*A61F 11/08* (2006.01)
*A61F 7/12* (2006.01)
*F26B 9/00* (2006.01)
*A61F 7/00* (2006.01)

(56) References Cited

U.S. PATENT DOCUMENTS

| | | | |
|---|---|---|---|
| 2004/0060192 A1* | 4/2004 | Gronka | A61F 11/006 34/90 |
| 2009/0041279 A1 | 2/2009 | Davis | |
| 2011/0099832 A1 | 5/2011 | Bikhazi | |
| 2015/0090191 A1 | 4/2015 | Kokenis | |
| 2018/0125345 A1 | 5/2018 | Rebella et al. | |

FOREIGN PATENT DOCUMENTS

| | | |
|---|---|---|
| DE | 69214690 T2 | 3/1997 |
| EP | 0243261 A1 | 10/1987 |
| EP | 0266383 A1 | 5/1988 |
| EP | 0937422 A2 | 8/1999 |
| WO | 0010627 A1 | 3/2000 |
| WO | 2012166801 A1 | 12/2012 |

OTHER PUBLICATIONS

Extended European Search Report Application No. 18183454.0 Completed: Dec. 20, 2019; dated Jan. 7, 2019 7 Pages.
Chinese Office Action; Application No. 201980052466.7; dated Sep. 22, 2021; 12 Pages.

* cited by examiner

ATTACHMENT FOR A DEVICE FOR GENERATING AN AIRFLOW

TECHNICAL FIELD

The present teaching relates to an attachment for a device for generating an airflow, preferably a warm airflow, or for delivering a fluid, which attachment is adapted to be inserted at least in sections into an external ear canal of a human or animal ear in order to dry moisture accumulations in the external ear canal.

Furthermore, the present teaching relates to an ear drying apparatus comprising a device for generating an airflow and the attachment according to the present teaching.

BACKGROUND

Patients suffering from chronic wet ear canals—whether due to a radical cavity, eardrum perforation or other external ear canal disease—or wearers of hearing aids are often confronted with the problem of efficiently removing moisture from the external ear canal. In addition, water can enter the ear canal in the bathtub, in the shower or while swimming, which can lead to reduced hearing. It also makes it easier for bacteria, germs and dirt to enter the external ear canal and cause inflammation, requiring rapid removal of these fluid accumulations.

However, no devices are known from the prior art, which allow such removal in a safe and efficient manner. For example, it is known to introduce an airflow into the ear canal through which the external ear canal is to be dried. An attachment insertable into the external ear canal for an airflow generating device is known from EP 0937422 B1. On the one hand, however, the proposed attachment directs the air introduced into the external ear canal directly onto the eardrum of the treated ear, which can result in injuries and permanent damage; on the other hand, due to its design, the attachment cannot be pushed into the ear canal of the patient or can only be pushed a few millimeters deep, so that in particular accumulations of moisture, which are located in the eardrum-side end region of the usually 2 to 2.5 cm long ear canal, cannot be removed or can only be removed after a longer period of application and/or higher intensity of the airflow.

Similarly, when the external ear canal is freed from cerumen by means of a fluid, injuries to the eardrum may occur if the fluid is directed directly to the eardrum. At the same time, cerumen residues may remain in the external ear canal and cleaning of the external ear canal may be unsatisfactory if the fluid cannot reach the entire external ear canal.

Injuries to the eardrum can also occur when a fluid is released into the external ear canal for the purpose of care or therapeutic treatment of the external ear canal when the fluid is directed directly to the eardrum. The caring or therapeutic effect of such treatment of the external ear canal with a fluid cannot reach its maximum if the fluid cannot reach the entire external ear canal.

SUMMARY

It is, therefore, an object of the present teaching to provide an attachment for a device for generating an airflow, preferably a warm airflow, which attachment enables rapid and efficient removal of moisture from the external ear canal of a human or animal by means of an airflow without exposing the eardrum to the risk of injury.

In addition, the attachment provided should be easily adaptable to different ear canals, have a simple design and be inexpensive to manufacture.

In addition, the efficiency of ear drying apparatuses, which include the attachment according to the present teaching, is to be significantly increased. The ear drying apparatus according to the invention should provide a noticeable drying result after only 15 seconds of use. Complete drying should be achieved by an application time of about 30 seconds or less.

In addition, it is an object of the present teaching to provide an attachment for a fluid delivery device, which attachment allows rapid and efficient removal of cerumen from the external ear canal of a human or animal by means of a fluid without exposing the eardrum to the risk of injury.

Finally, it is an object of the present teaching to provide an attachment for a fluid delivery device, which attachment enables rapid and efficient care or therapeutic treatment of the external ear canal of a human or animal by means of a fluid without exposing the eardrum to the risk of injury.

A problem underlying the present teaching is solved in accordance with the invention by an attachment for a device for generating an airflow, preferably a warm airflow, which attachment is adapted to be introduced at least in sections into an external ear canal of a human or animal ear, wherein the attachment has a connecting piece for connection to the device for generating an airflow, and a guide vane of tongue-like design for guiding air flowing out of the device for generating an airflow, having a guide vane base, and wherein the guide vane base of a first section of the guide vane has a longitudinal cross-sectional profile, which is curved in a first direction, and the guide vane base of a second section of the guide vane has a longitudinal cross-sectional profile, which is curved in a second direction, and the two curved sections extend in an adversely curved manner to one another. The connecting piece can thereby be designed in various ways. For example, it can form an essential element of the attachment and give it stability. However, it may also be only a section of the attachment which allows the attachment to be connected to the airflow generating device without significantly contributing to the stability of the attachment.

In accordance with the present teaching, the airflow provided by the device for generating an airflow is introduced into the external ear canal via the attachment in accordance with the present teaching and is guided by the guide vane in such a way that a particularly advantageous flow for the desired drying is created within the external ear canal. The airflow flows into the attachment via the connecting piece, flowing first through the connecting piece and then being guided via the guide vane base of the guide vane in the direction of the external ear canal. Due to the course of the guide vane according to the present teaching and as a result of the curvature of the guide vane base, a particularly favorable flow distribution of the airflow within the external ear canal is achieved. Particularly in comparison with attachments whose guide vane base shows a straight progression of the longitudinal cross-section, particularly good drying results could be achieved. It is particularly advantageous if—as viewed from the connecting piece—the pitch of a tangent applied to the guide vane base decreases in the first section of the guide vane base with the distance from the connecting piece and increases in the second section of the guide vane base with the distance from the connecting piece. The airflow is directed by the attachment according to the present teaching in such a way that a vortex field forms approximately inside the external ear canal. Depending on the extent to which the attachment is inserted into the user's external ear canal, this vortex field may be caused either by a swirl experienced by the airflow due to the guide vane and/or by reflection of the airflow from the eardrum-facing side walls of the external ear canal. This means that the airflow cannot hit the eardrum directly, but can only be reflected onto the side walls of the external ear canal and, preferably several times, on these side walls before said airflow is directed along the eardrum so that it strokes along its surface. For example, the airflow can strike an upper side wall of the ear canal, be reflected there, and be directed along the eardrum toward a lower side wall of the external ear canal, where the airflow is reflected once again and is finally conveyed toward the auricle. It is also possible for the airflow to be reflected several times by the side walls of the external ear canal before it reaches the eardrum. In particular, moisture accumulations can also be removed from the recessus meatus acustici externi by means of the attachment according to the present teaching—i.e. the trough which occurs directly in front of the eardrum between the downward sloping floor of the external ear canal and the sloping eardrum covering this floor. The turbulence of the airflow, whether caused by the swirling and/or reflection from the side walls of the external ear canal leading to the eardrum, causes the airflow to sweep over the eardrum and the recessus meatus acustici externi, but does not strike the eardrum frontally. Due to the flow of air inside the external ear canal, which is caused by the attachment according to the present teaching, there are particularly short application times, which are necessary for satisfactory drying. For example, a noticeable drying effect can already be observed after 15 seconds, if an ear drying apparatus according to the present teaching—as described below—is used with the attachment according to the present teaching. To completely dry the external ear canal—i.e. to reduce the moisture content in the ear canal back to the usual level—an application time of about 30 seconds or less is sufficient.

In addition, it has been shown that the attachment according to the present teaching also allows a particularly gentle and at the same time effective removal of cerumen from the external ear canal when the attachment is used in conjunction with a device for dispensing a fluid. Due to the guide vane according to the present teaching, the fluid, e.g. water, forms a particularly favorable flow path inside the external ear canal for cleaning. Analogous to the airflow described above, the fluid is also forced into an approximate vortex field when it flows into the external ear canal, so that on the one hand a direct impact of the fluid on the eardrum is prevented and on the other hand a particularly effective removal of cerumen from the external ear canal, in particular of cerumen adhering to the side walls, is achieved simultaneously by the vortexing and/or reflection of the fluid on the side walls of the external ear canal.

It has also been shown that the attachment according to the present teaching also enables particularly gentle and at the same time effective nurturing or therapeutic treatment of the external ear canal if the attachment is used in conjunction with a device for dispensing a fluid. Due to the guide vane according to the present teaching, the fluid inside the external ear canal forms a flow pattern which is particularly favorable for the nurturing or therapeutic treatment of the external ear canal. Injuries to the eardrum can be avoided and the nurturing or therapeutic effect maximized, as the fluid used for the nurturing or therapeutic treatment is not directed directly onto the eardrum and can reach the side walls of the external ear canal particularly well due to the turbulence and/or reflection of the fluid according to the present teaching.

In accordance with a preferred embodiment of the present teaching, it is provided that the first section and the second section are to converge immediately into each other. In particular, it is favorable from a fluidic point of view if the first section and the second section of the guide vane base are not separated from each other by a discontinuity but merge smoothly into each other.

This leads to a flow of air within the external ear canal which is particularly favorable for the desired drying effects.

While it is in principle sufficient to introduce the tongue-like guide vane into the external ear canal and exploit either the turbulence of the airflow caused by the guide vane or the reflection and/or turbulence on the walls of the external ear canal also caused by the guide vane in order to achieve the effect described above, which is in accordance with the present teaching and permits gentle drying of the eardrum, it may be advantageous to additionally provide an ear funnel for the attachment.

According to another preferred embodiment of the attachment according to the present teaching, it is therefore provided that the attachment comprises an ear funnel, which ear funnel encloses the tongue-like guide vane at least in sections, preferably completely, along its length and has a proximal opening.

The ear funnel serves as that part of the attachment which is brought into direct contact with the external ear canal or side walls thereof when the attachment is used as intended and inserted into the user's external ear canal. The ear funnel can connect to the connecting piece of the attachment and project from it, or the connecting piece can form an end section of the ear funnel. The guide vane is arranged at least in sections within the ear funnel, preferably in the form of a sleeve. Preferably the guide vane does not protrude from the ear funnel. The ear funnel allows, on the one hand, a slight widening and an advantageous positioning for drying—namely a slight straightening—of the usually obliquely extending external ear canal when the attachment with the ear funnel is inserted into the external ear canal of a human or animal; on the other hand, the ear funnel also allows a simple adaptation of the attachment to different conditions, such as the application in adults or children—for example by appropriate choice of shape and size of the ear funnel. The length of the ear funnel can be adjusted to the length of the guide vane in order to support the formation of the turbulences and reflections described above in the external ear canal. When the attachment is used as intended to dry the external ear canal, it is inserted into or attached to the user's external ear canal with the proximal opening of the ear funnel. The term proximal refers in this case and below to the position of a certain element relative to the eardrum of the user. Specifically, the proximal opening means the opening of the ear funnel closest to the eardrum of the user.

In another preferred embodiment of the attachment according to the present teaching, it is provided that, when considering a longitudinal cross-section of the attachment, the guide vane base intersects a longitudinal axis of the attachment, which longitudinal axis passes through the center point of a cross-section of the connecting piece normal to the longitudinal cross-section.

The tongue-like guide blade of the attachment intersects the longitudinal axis extending through the center of the cross-section of the connecting piece. According to the present teaching, this presupposes that the guide vane, in a side view of the attachment, extends at least in sections diagonally to this longitudinal axis. Preferably, the guide vane can have a non-vanishing gradient over its length in the direction of flow. The fact that the guide vane, in particular the longitudinal cross-section of the guide vane base, intersects the longitudinal axis of the attachment means that the airflow is directed in such a way that it does not strike the user's eardrum directly.

According to another preferred embodiment, of the attachment according to the present teaching, it is intended that, when viewing a longitudinal cross-section of the attachment, the guide vane base intersects a longitudinal axis of the ear funnel, which longitudinal axis runs through the center point of the proximal opening of the ear funnel.

If the ear funnel is rotationally symmetrical—which is preferably the case apart from an outlet opening in the jacket of the ear funnel—the longitudinal axis of the ear funnel coincides with its axis of rotation. The guide vane can be arranged inside the ear funnel in such a way that, when viewed in a longitudinal section, the guide vane base intersects the longitudinal axis of the ear funnel, wherein it has proven to be particularly effective for the turbulences or reflections to be achieved and thus for the drying to be achieved if the guide vane base intersects the longitudinal axis of the ear funnel in a proximal end region of the ear funnel.

Preferably, the longitudinal axis of the ear funnel coincides with the longitudinal axis of the attachment. This makes it possible to keep the structure of the attachment according to the present teaching particularly simple.

According to another preferred embodiment of the attachment according to the present teaching, it is provided that the tongue-like guide vane has two guide vane cheeks protruding from the base of the guide vane, namely a first guide vane cheek and a second guide vane cheek, wherein the guide vane base and the guide vane cheeks form a guide channel or part of a guide channel for the air flowing out of the device for generating an airflow.

The guide vane cheeks ensure targeted and controlled guidance of the airflow along the guide vane and controlled delivery of the airflow to the external ear canal. Also, in the case of embodiments of the attachment with ear funnel, any unwanted reflections of the airflow on an inner wall of the ear funnel can be avoided. The guide vane cheeks can contact the ear funnel over the entire length of the guide vane base, for example, or only in one or more longitudinal sections of the guide vane base. Alternatively, the guide vane cheeks can also be spaced from the ear funnel.

According to another preferred embodiment it is provided that the first guide vane cheek projects from a first longitudinal edge of the guide vane base and the second guide vane cheek projects from a second longitudinal edge of the guide vane base opposite the first longitudinal edge. Alternatively, it may also be provided that the first guide vane cheek is formed by the first longitudinal edge of the guide vane base and the second guide vane cheek is formed by the second longitudinal edge of the guide vane base.

The guide vane cheeks delimit the guide vane base on its mutually opposite longitudinal sides and largely prevent the airflow used for drying from the guide channel from reaching other areas of the attachment, such as an exhaust air channel, before it reaches the external ear canal for proper drying. If, on the other hand, the guide vane cheeks contact the ear funnel over their entire length, this overflow of air from the guide channel to other areas, such as the exhaust air channel, can be completely prevented. In this way, the guide vane can be used to isolate or separate the guide channel and the exhaust air channel fluidically from each other. Particularly advantageous drying effects can be achieved if the guide vane cheeks run along the entire length of the guide vane. The guide vane cheeks may also be produced integrally with the guide vane base and may be formed by the first longitudinal edge and the second opposite longitudinal edge of the guide vane base. The guide vane cheeks may have a cross-sectional profile with different curvature compared to the guide vane base located between the guide vane cheeks. The transition between the guide vane base and the guide vane cheeks can be smooth and can only be expressed by a change in the slope or curvature of the cross-sectional profile of the guide vane base. This can make it difficult to make a clear distinction between the guide vane base and the guide vane cheeks. For example, the guide vane base and guide vane cheeks can be arranged in such a way that an overall cross-section of the guide vane formed by the guide vane base and guide vane cheeks is essentially U-shaped.

According to another preferred embodiment of the attachment according to the present teaching, it is provided that the tongue-like guide vane protrudes from the connecting piece and preferably has a section running in the connecting piece.

This is particularly advantageous if the attachment has no or a removable ear funnel. The connecting piece in this case serves on the one hand to connect to the device for generating the airflow but on the other hand also gives the attachment the necessary stability to support the guide vane.

In order to prevent injuries to the eardrum and/or the sidewall of the external ear canal, another preferred design of the attachment according to the present teaching is that the tongue-like guide vane is arranged completely within the ear funnel and/or the connecting piece.

Attachments according to this embodiment of the present teaching minimize the risk of injury to the eardrum and/or side walls of the user's external ear canal because the entire guide vane is concealed inside the attachment. In particular, the first and second sections of the guide vane may be located within the ear funnel and the section of the guide vane within the connecting piece may be located within the connecting piece.

According to another preferred embodiment of the attachment according to this present teaching, it is provided that the ear funnel tapers from the connecting piece to the proximal opening of the ear funnel.

The proximal opening preferably has a circular circumference and a diameter not exceeding 7 mm. As the shape of the ear funnel is adapted to the shape of the external ear canal at least in the proximal end area of the ear funnel, which proximal end area is inserted into the ear canal, this allows a particularly simple and painless insertion of the attachment into the external ear canal. The attachment according to the present teaching can thus be brought to a distance of up to about 20 mm, preferably 15 mm, especially preferably 10 mm, from the eardrum of the user, which supports the formation of the approximate vortex field in the external ear canal described above and can promote the drying of fluid accumulations in the recessus meatus acustici externi. The achievable minimum distance from the eardrum may vary depending on the specific suitability of the attachment for use on men, women or children.

Preferentially, a proximal end of the guide vane, preferably a proximal end of the guide vane base, is arranged substantially flush with the proximal opening of the ear funnel.

In such embodiments of the present teaching, the guide vane is essentially flush with the ear funnel. This allows the airflow to be particularly well directed through the proximal opening of the ear funnel into the external ear canal as it exits the attachment. Both an outlet angle, at which the airflow—relating to the longitudinal axis of the ear funnel or the attachment—flows out of the attachment, and a swirl, which is to be added to the airflow when it exits the attachment, can be adjusted particularly well with this embodiment. In particular, an angle of incidence at which the airflow hits the side walls of the external ear canal can be predetermined even better.

According to another preferred embodiment of the attachment according to the present teaching, it is provided that the proximal end of the guide vane, preferably a proximal end of the guide vane base, subdivides the proximal opening of the ear funnel into an outflow opening for air flowing from the attachment into the ear canal and an inflow opening for air flowing from the ear canal into the attachment.

The proximal opening of the ear funnel is thus used on the one hand for the dry airflow, preferably warm airflow, which is used for drying, from the attachment to flow into the external ear canal—namely in the area of the outflow opening; on the other hand, moist air from the external ear canal can also flow back into the attachment via the proximal opening—namely in the area of the inflow opening. The ear funnel thus also allows the air used for drying to flow out of the ear canal and prevents the formation of a backflow within the ear canal. Humid air can, therefore, leave the external ear canal immediately after absorbing moisture and isolated from the side walls of the external ear canal, resulting in an improved drying effect. This ensures that the airflow used for drying in the area of the proximal opening is not mixed with moist air before being introduced into the external ear canal. In this case, the proximal end of the guide vane or the proximal end of the guide vane base and/or the guide vane cheeks contacts an inside of the ear funnel to fluidly separate the inlet and outlet openings.

According to another preferred embodiment of the present teaching, it is provided that the tongue-like guide vane divides an inner volume of the ear funnel into a supply air channel for air flowing from the attachment into the ear canal and an exhaust air channel for air flowing from the ear canal into the attachment, wherein preferably the supply air channel connects the connecting piece to the outlet opening and wherein preferably the exhaust air channel connects the inflow opening to an outlet of the attachment.

This means that the dry airflow and the moist air exiting from the external ear canal can mostly be guided separately from each other in the attachment. The dry airflow, preferably warm airflow, is first generated by the device for generating an airflow, is guided through the connecting piece and via the guide vane via the supply air channel of the ear funnel and into the external ear canal. After drying of the external ear canal, in particular the recessus meatus acustici externi, the moist air can leave the external ear canal via the inflow opening and is led via the exhaust air canal to the outlet of the ear funnel, via which outlet the moist air is expelled from the attachment. This means that there is no or very little mixing of the air masses in the supply air channel and the exhaust air channel within the attachment, which further increases the efficiency of the drying process.

In general, the guide vane base or guide vane cheeks can contact the ear funnel, especially the inside of the ear funnel, either at no point or over the entire length of the ear funnel or only in the area of the proximal opening of the ear funnel. There are also possible embodiment variants in which the guide vane base or the guide vane cheeks contact the ear funnel in sections and are spaced in sections from the ear funnel, namely its inner side.

According to another preferred embodiment, it is provided that a cross-section of the supply air channel decreases in the direction of flow.

The flow direction is the direction in which the airflow flows through the supply air channel to enter the external ear canal. This cross-sectional narrowing of the supply air channel, which is preferably formed continuously, allows the outlet speed at which the airflow leaves the attachment to be set and an outlet speed that is particularly advantageous for the desired drying effect to be selected.

The attachment is dimensioned so that the outlet of the attachment lies outside the external ear canal. In this case, the outlet is preferably formed by an opening in a housing wall of the ear funnel, preferably in a section of the ear funnel directly upstream of the connecting piece.

The moist air, which has already been used for drying, is no longer introduced into the connecting piece or even into the device for generating an airflow but leaves the attachment already in the area of the ear funnel. This results in a further simplification of the structure of the attachment and also of the device for generating an airflow. Overall, this measure can keep the production costs of the attachment low. The outlet can also be manufactured in a particularly simple manner by arranging the outlet in the section of the ear funnel upstream of the connecting piece. In this case, the outlet is located in a section of the ear funnel which, when used as intended, protrudes at least partially, preferably completely, from the user's external ear canal.

In accordance with the present teaching, the attachment can also be designed in such a way that the connecting piece and the guide vane are integrally formed with each other and can preferably be connected as a unit to the ear funnel, or that the ear funnel and the guide vane are integrally formed with each other and can preferably be connected as a unit to the connecting piece, or that the connecting piece, the guide vane and the ear funnel are formed in one piece with each other.

In the case of the integral design of connecting piece and guide vane, differently formed ear funnels can be used in conjunction with one and the same unit comprising the connecting piece and the guide vane, which unit can then be offered as a separate spare part. This means that the attachment can be adapted to different ear canals without having to replace the connecting piece or the guide vane. This is particularly advantageous for the reason that the design of the connecting piece depends primarily on the size and shape of an outlet opening for the airflow of the device for generating an airflow and is thus adapted to the device used in each case. This means that the ear funnel can be specially adapted to the respective user group independently of the other components of the attachment. For example, material, size and/or shape of the ear funnel can be selected depending on whether the attachment is to be used by female or male adults or children, while the remaining components of the attachment are adapted to the respective device for generating an airflow in conjunction with which the attachment is to be used. Thus the ear funnel is easily exchangeable and can be retrofitted independently of the other components of the attachment. The possibility of replacing the ear funnel after each treatment of the ear is also very beneficial from a hygienic point of view.

In the case of the integral design of the ear funnel and guide vane, all parts of the attachment which, when used as intended, (can) come into contact with the external ear canal of the user, namely the ear funnel and guide vane, may be offered as separate spare parts and connected to the connecting piece. This enables a particularly hygienic use of the attachment according to the present teaching, as the unit comprising the ear funnel and the guide vane can be replaced after each application.

In the case of the integral design of the ear funnel, guide vane and connecting piece, the entire attachment can be offered as a separate spare part and replaced after each application. This embodiment is also very cost-effective.

According to a further embodiment, it is intended that the connecting piece is formed by an end section of the ear funnel.

Particularly in the case of an integral design of ear funnel, guide vane and connecting piece, the attachment according to the present teaching can be made more compact and less expensive by eliminating the need for an additional separate component.

The object underlying the present teaching is also solved by an ear drying apparatus comprising a device for generating an airflow, preferably a warm airflow, and an attachment according to the teaching and according to the previously described embodiments.

BRIEF DESCRIPTION OF THE DRAWINGS

The present teaching is now explained in more detail using embodiment examples. The figures are exemplary and are supposed to present the idea of present teaching, but in no way restrict it or even finally reproduce it, wherein:

FIG. 7a shows a line representation of FIG. 1a;
FIG. 7c shows a line representation of FIG. 2a.

DETAILED DESCRIPTION

In the following description, the term "longitudinal section" means a section through an attachment 1 according to the present teaching in which the section plane is parallel to the drawing plane of the figures and a longitudinal axis 12 of the attachment 1 lies in the section plane. In addition, the term "cross-section" means a section through attachment 1 in which the plane of the section is orthogonal to the longitudinal section.

In principle, there is a large number of conceivable embodiments of the attachment according to the present teaching, wherein all these embodiments have in common that an airflow is swirled by a guide vane and/or is reflected due to the guide vane geometry on side walls of an external ear canal 3 of a user in order to effect an optimum drying effect inside the external ear canal 3.

In a first embodiment, the attachment 1 according to the present teaching comprises a connecting piece 4 and a tongue-like guide vane 5, and can in addition optionally comprise an ear funnel 18, wherein the connecting piece 4 and the guide vane 5 are formed integrally with one another and can be detachably connected to the ear funnel 18. This embodiment is characterized in that, inter alia, the ear funnel 18 can be removed and the attachment 1 can be used with or without the ear funnel 18. The ear funnel 18, which is not mandatory for this embodiment, can be easily replaced, if present, and can be retrofitted independently of the connecting piece 4 and the guide vane 5. The possibility of changing the ear funnel 18 after each drying process is also very favorable from a hygienic point of view.

In a second embodiment, the attachment according to the present teaching also comprises the connecting piece, the guide vane and the ear funnel, wherein the ear funnel and the guide vane are integrally formed with each other in this embodiment and the unit of ear funnel and guide vane are connectable to the connecting piece. All parts of the attachment which (can) come into contact with the external ear canal 3 of the user when the attachment is used as intended, namely the ear funnel and guide vane, can be offered as separate spare parts and connected to the connecting piece. This enables a particularly hygienic use of the attachment according to the present teaching, as the unit comprising the ear funnel and the guide vane can be replaced after each application.

In a third embodiment, the attachment according to the present teaching also includes the connecting piece, the guide vane and the ear funnel, wherein the connecting piece, the guide vane and the ear funnel are formed integrally with each other in this embodiment. This means that the entire attachment can be offered as a separate spare part and replaced after each application. This results in a particularly simple and hygienic handling of the attachment according to the third embodiment. In addition, the attachment can be manufactured particularly easily and thus inexpensively due to its integral design.

Also included in the inventive idea are the embodiments of the attachment in which the connecting piece, the guide vane and the ear funnel are each designed as separate components.

In the following, the present teaching is described in more detail using the first embodiment of the attachment 1 according to the present teaching as depicted in FIGS. 1 to 6; the second and third embodiments, however, are not depicted in FIGS. 1 to 6.

Figure 1A:
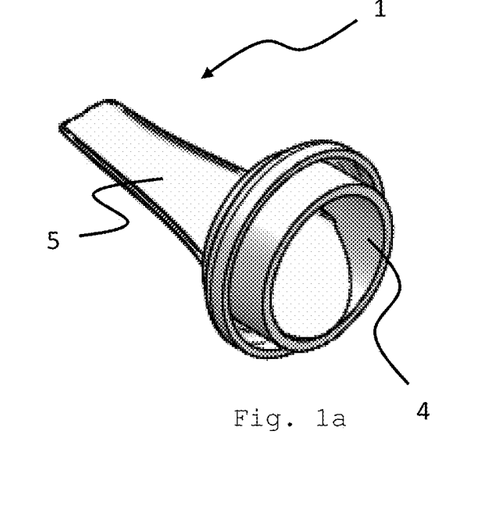
FIG. 1a shows an attachment according to the present teaching in a first embodiment.

FIG. 1a is a perspective representation of this embodiment of the attachment 1 according to the present teaching without ear funnel, which is optional for this embodiment. Attachment 1 comprises the connecting piece 4 for connecting attachment 1 to a device 2 for generating an airflow, preferably a warm airflow.

The connecting piece 4 forms the section of the attachment 1, which ensures that the attachment 1 holds on to the device 2 for generating an airflow.

Furthermore, attachment 1 comprises the tongue-like guide vane 5, which can be inserted into an external ear canal 3 of an animal or human (hereinafter referred to as the user) for the purpose of drying the ear canal 3 (see FIG. 6). The guide vane 5 allows controlled guidance of the airflow and its controlled release to the external ear canal 3. The guide vane 5 has a guide vane base 25 to guide the airflow and can also include guide vane cheeks 26 to form a guide channel or part of a guide channel for the airflow.

Figure 3A:
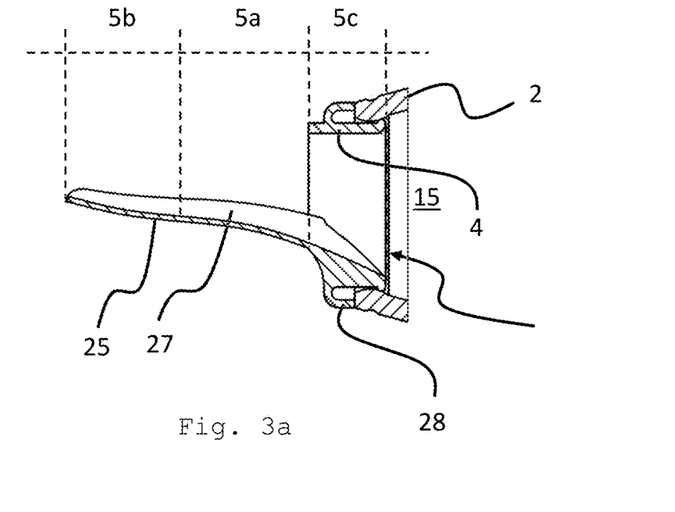
FIG. 3a shows a longitudinal sectional view through the attachment of FIGS. 2a and 2b, which is fastened to a device for generating an airflow.
Figure 3B:
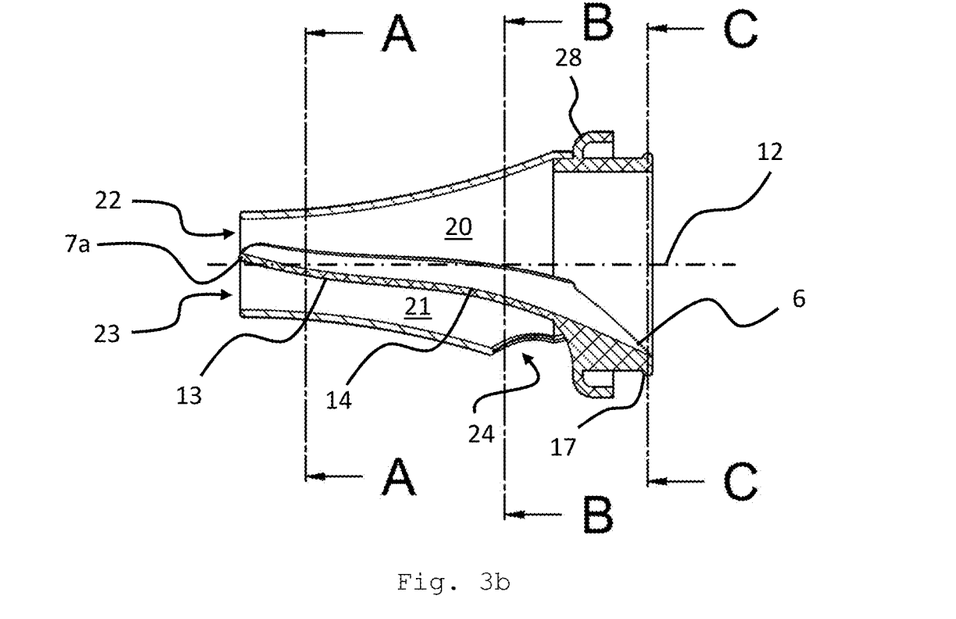
FIG. 3b shows a longitudinal sectional view through the attachment of FIGS. 2a and 2b.

FIG. 3a shows a longitudinal section of the attachment 1 according to the present teaching and according to the first embodiment without ear funnel, which longitudinal section runs through the connecting piece 4 and the guide vane 5. FIG. 3b shows the attachment 1 from FIG. 3a with ear funnel 18, wherein the attachments 1 shown in FIGS. 3a and 3b are identical except for the ear funnel 18.

The essentially sleeve-shaped connecting piece 4 serves to connect the attachment 1 to the device 2 for generating an airflow and enables the airflow from the device 2 to flow into the attachment 1. The geometry of the connecting piece 4 is determined by the geometry of an outlet opening 15 of the device 2 for generating an airflow, through which outlet opening 15 the airflow flows out of the device 2. In the embodiment example shown, the tongue-like guide vane 5 protrudes away from the connecting piece 4 and deflects the airflow into the external ear canal 3 of the user (see FIG. 6).

In order to be able to use the attachment 1 illustrated in FIG. 3a for drying the external ear canal 3 as intended, it can be inserted with the guide vane 5—either in sections or completely—into the external ear canal 3 of the user.

FIGS. 3a and 3b clearly show that the guide vane 5 is arranged in such a way that the guide vane base 25 intersects the longitudinal axis 12 of the attachment 1. The longitudinal axis 12 of attachment 1 extends through a center point of a cross-section of the connecting piece 4 which is normal to the longitudinal section shown in FIGS. 3a and 3b. The cross-section of the connecting piece 4 refers exclusively to the connecting piece 4 itself—in particular therefore not to any sections of the guide vane 5 arranged within the connecting piece 4. The cross-section of the connecting piece 4, through the center point of which the longitudinal axis 12 extends, is shown in FIG. 4c.

As a result of this arrangement of the guide vane 5, the airflow is introduced into the external ear canal 3 of the user in such a way that in the external ear canal 3 a flow field is created which is particularly advantageous for the desired drying effect. This also ensures that the airflow exiting attachment 1 is not directed directly to the user's eardrum 31. The airflow is swirled and/or introduced into the external ear canal 3 when it passes over a proximal end 7a of the vane bottom 25 and leaves the attachment 1 in such a way that the airflow is reflected at the side walls of the external ear canal 3 to provide an optimal drying effect inside the external ear canal 3. Preferably, the guide vane base 25 intersects the longitudinal axis 12 in a proximal end area of the attachment 1, which is closest to the user's eardrum 31.

Figure 4A:
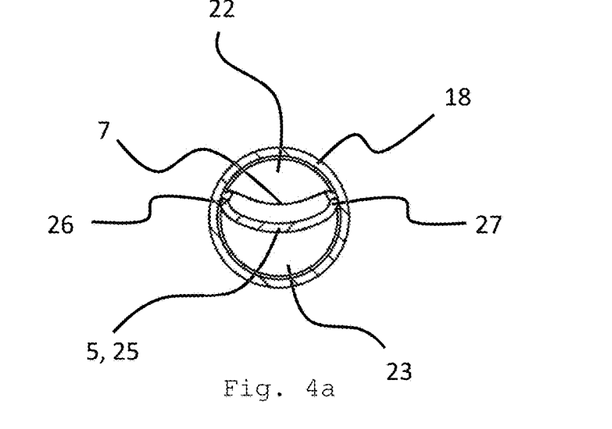
FIG. 4a shows a cross-sectional view of the attachment of FIG. 3b according to A-A.
Figure 4B:
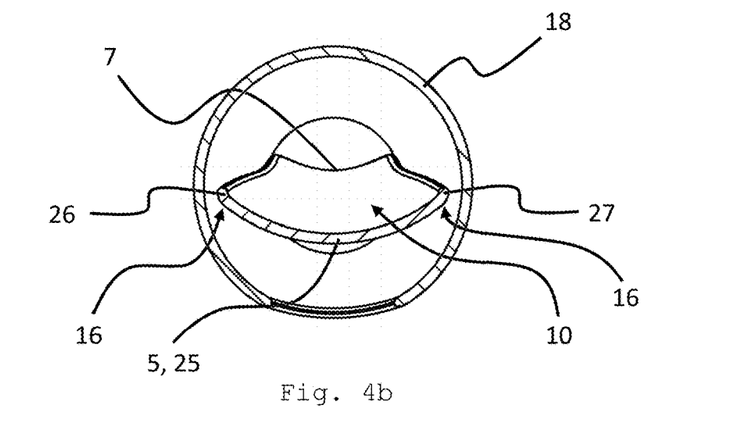
FIG. 4b shows a cross-sectional view of the attachment of FIG. 3b according to B-B.
Figure 4C:
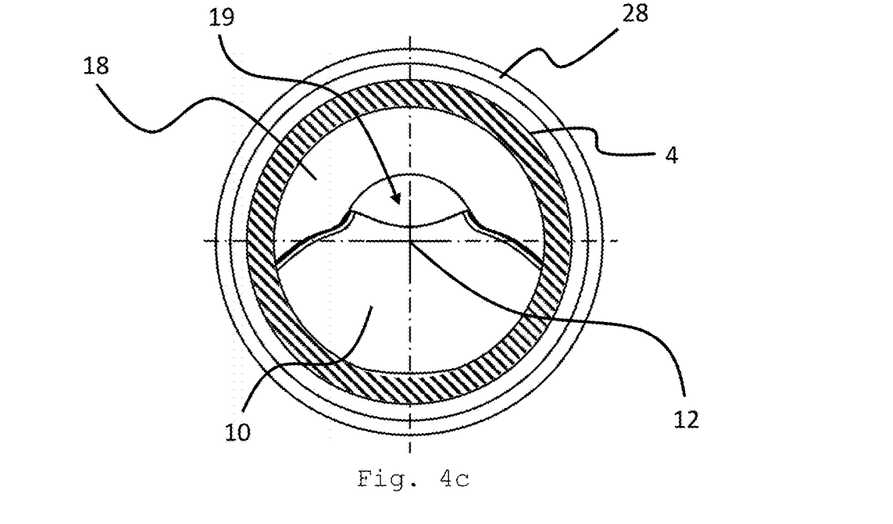
FIG. 4c shows a cross-sectional view of the attachment of FIG. 3b according to C-C.

It can also be seen from FIGS. 3a and 3b that the guide vane base 25 has a curved longitudinal section which stands in a normal manner on the cross-section of the guide vane base 25 as illustrated in FIGS. 4a and 4b. The guide vane base 25 of a first section 5a of the guide vane 5 projecting from the connecting piece 4 has a longitudinal cross-sectional shape curved in a first direction, and the guide vane base 25 of a second section 5b of the guide vane 5 projecting from the connecting piece 4 has a longitudinal cross-sectional shape curved in a second direction, wherein the two curved sections 5a, 5b extend in a curved manner opposite to each other. In the embodiment example shown in FIGS. 3a and 3b, the second section 5b has a proximal end 7 of the guide vane 5.

Thus the guide vane 5 comprises at least a first apex 13 and a second apex 14. This special course of the guide vane 5 results in a particularly favorable flow distribution of the airflow within the external ear canal 3. With this embodiment of the present teaching, particularly good drying results could be achieved, especially in comparison with attachments comprising a guide vane 5 with a straight longitudinal cross-section. It is particularly advantageous if—viewed from the connecting piece 4—the gradient of a tangent applied to the guide vane base 25 decreases in the first section 5a of the guide vane base 25 with the distance from the connecting piece 4 and increases in the second section 5b of the guide vane base 25 with the distance from the connecting piece 4.

The guide vane 5 has a section 5c extending in the connecting piece 4, wherein section 5c has a distal end 6 of the guide vane 5 because it is remote from the user's eardrum 31. Section 5c adjoins section 5a of guide vane 5. A flow cross-section for air flowing from the device 2 for generating an airflow into the attachment 1 is limited by the section 5c of the guide vane 5 extending in the connecting piece 4 and the connecting piece 4. This makes it possible to adjust the proportion of the total airflow which should pass unhindered from the connecting piece 4 to the guide vane 5. In particular, the airflow can also be subjected to a flow cross-section constriction, which can be less drastic with attachments for children, for example, than with attachments for adults. The section 5c of the guide vane 5 running in the connecting piece 4 also makes it possible to take up the airflow flowing from the device 2 for generating an airflow into the attachment 1 already in the area of the connecting piece 4, so that the airflow can be directed accordingly as soon as it enters the attachment 1.

From the longitudinal edges 16 of the guide vane base 25, two guide vane cheeks, namely a first guide vane cheek 26 and a second guide vane cheek 27, project from the guide vane base 25 to form, together with the guide vane base 25, a guide channel 10 or part of a guide channel 10 for the airflow. Guide vane base 25 and guide vane cheeks 26, 27 form part of guide channel 10 if the guide vane cheeks 26, 27 only project from the guide vane base 25 in one longitudinal section of guide vane 5 but not over its entire length. The guide channel 10 for the airflow, formed by the guide vane base 25 and the guide vane cheeks 26, 27, is formed by that volume which is limited by the guide vane base 25, the first guide vane cheek 26 on the one hand, and the second guide vane cheek 27 on the other hand. The guide channel 10 further improves the targeted and controlled guidance of the airflow within the attachment 1 and the controlled delivery of the airflow to the external ear canal 3. In the case of embodiments with an ear funnel, such as the first embodiment of attachment 1 with an ear funnel 18 as shown in FIG. 3b, the use of guide vane cheeks 26, 27 can also prevent any unwanted reflections of the airflow on an inner wall of the ear funnel 18.

FIG. 4a shows the cross-section of the attachment 1 according to the present teaching according to intersecting line A-A from FIG. 3b. FIG. 4b shows the cross-section according to intersecting line B-B from FIG. 3b. In both cases the section runs through the ear funnel 18 and through the guide vane base 25 of the guide vane 5. FIG. 4c shows the cross-section of the connecting piece 4 according to the intersecting line C-C from FIG. 3b.

As can be seen in FIGS. 4a, 4b, the guide vane base 25 in the embodiment example shown has a curved cross-sectional profile, preferably U-shaped. The cross-section of the guide vane base 25 is curved, in a slightly U-shaped manner, over the entire length of the guide vane 5. The curvature can increase or decrease from one end of guide vane 5 to the other end of guide vane 5. It may also be provided that the cross-section of the guide vane base 25 is not curved over the entire length of the guide vane 5, but only in one longitudinal section of the guide vane 5. Other than U-shaped curvatures of the cross-section profile of the guide vane base 25 are also conceivable. FIGS. 4a and 4b show cross-sections of attachment 1 with ear funnel 18 as shown in FIG. 3b. Since the attachment 1 shown in FIG. 3b, apart from the ear funnel 18, is identical to the attachment 1 shown in FIG. 3a, the statements made with regard to the curved cross-sectional profile of the guide vane base 25 also apply to the first embodiment of attachment 1 without ear funnel 18 as shown in FIG. 3a.

The attachment 1 according to the first embodiment may be inserted into the external ear canal 3 with or without ear funnel 18 in order to be used as intended for drying the external ear canal 3.

Figure 1B:
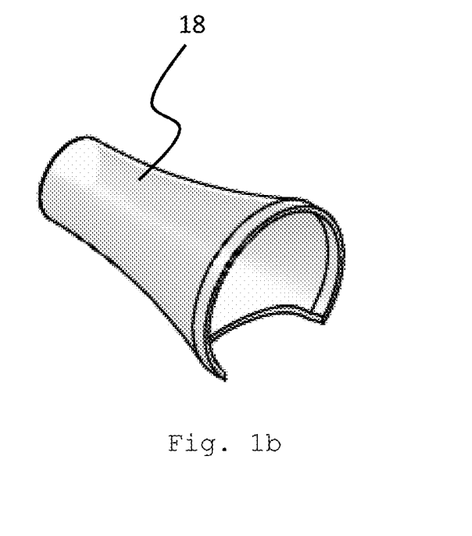
FIG. 1b shows an ear funnel of the first embodiment of the attachment according to the present teaching.
Figure 2A:
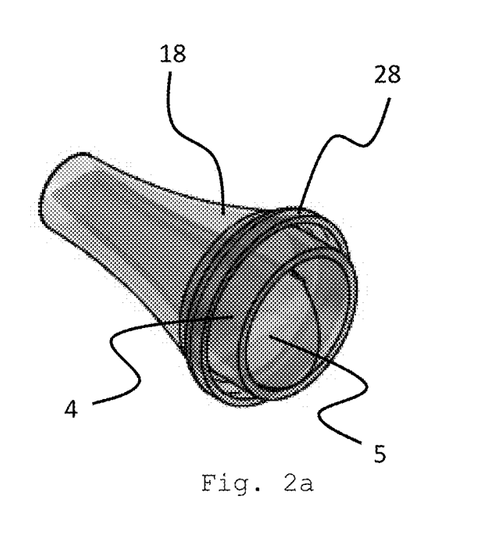
FIG. 2a shows the first embodiment of the attachment with the ear funnel in a first perspective view.
Figure 2B:
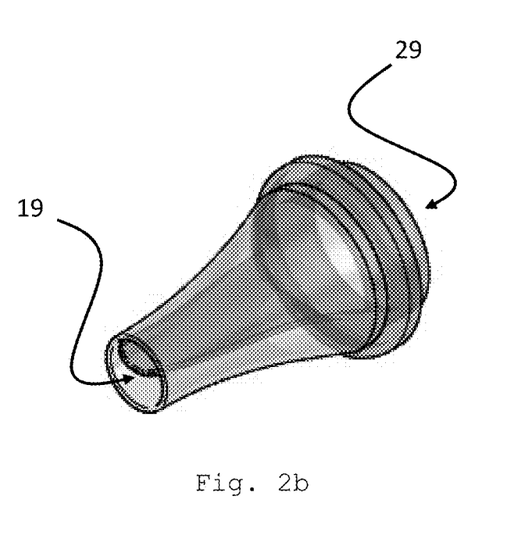
FIG. 2b shows the first embodiment of the attachment with the ear funnel in a second perspective view.

The attachment 1 shown in FIGS. 2a, 2b and 3b is obtained by detachably connecting attachment 1 shown in FIGS. 1a and 3a with the ear funnel 18 shown in perspective in FIG. 1b, namely attachment 1 according to the first embodiment with ear funnel 18. For this purpose, the ear funnel 18 can be pushed onto the connecting piece 4—or otherwise connected to said connecting piece or the guide vane. In other embodiments of attachment 1, such as the third embodiment described above, the connecting piece 4 can be passed through an end section, preferably a distal end section of the ear funnel 18.

In the case of the first embodiment of attachment 1 with ear funnel 18, the ear funnel 18 is detachably connectable to and protrudes from the connecting piece 4 in such a way that the guide vane 5 is encased along its entire length by the ear funnel 18 and the connecting piece 4 connected to it. Ear funnel 18 and connecting piece 4 may also be provided to encase only a longitudinal section of guide vane 5 so that guide vane 5 protrudes beyond ear funnel 18. The ear funnel 18 shown in FIG. 1b is rotationally symmetrical in the present embodiment example except for one outlet 24, wherein the longitudinal axis 12 of the attachment 1 forms the corresponding axis of rotation of the ear funnel 18.

FIGS. 2a, 2b, 3b, 4a, 4b and 4c clearly show that the cross-section of the ear funnel 18 decreases from the connecting piece 4 to a proximal opening 19 of the ear funnel 18, by means of which the ear funnel 18 is inserted into the ear canal 3 when the attachment 1 is used as intended. This reduction in cross-section makes it possible to determine the insertion depth of attachment 1 into the external ear canal 3. This makes it possible, for example, to move attachment 1 up to about 15 mm, preferably up to about 10 mm, to the eardrum 31 of the user.

The proximal end 7 of guide vane 5, or the proximal end 7a of guide vane base 25, is substantially flush with the proximal opening 19 of the ear funnel 18. Accordingly, the proximal end 7a of the vane base 25 is located within the proximal opening 19 of the ear funnel 18 and divides it into an outflow opening 22 for air flowing from the attachment into the external ear canal 3, and an inflow opening 23 through which inflow opening 23 air can flow from the external ear canal 3 back into the attachment 1.

In the case of embodiments of the attachment with ear funnel, for example in the case of the first embodiment of the attachment 1 with ear funnel 18, in which the guide vane 5 protrudes from or is connected to the connecting piece 4 of the attachment 1, the guide vane 5 extends substantially over the entire length of the ear funnel 18. This allows the airflow used for drying to be guided along the entire length of the ear funnel 18 and released into the external ear canal in a very controlled manner without risking injury to the external ear canal 3 and/or the eardrum.

To further increase the drying efficiency, the outflow opening 22 can be smaller than the inflow opening 23. For example, the outflow opening 22 can occupy one third of the proximal opening 19 and the inlet opening 23 two thirds of the proximal opening 19.

Since the proximal opening 19 of the ear funnel 18 is usually smaller than a distal opening 29 of the connecting piece 4, drying is further supported by the airflow by increasing the exit velocity of the airflow from attachment 1 and ensuring a particularly rapid and complete escape of the moist air from the ear canal 3. The airflow from device 2 flows into attachment 1 via the distal opening of connecting piece 4.

In embodiments of the attachment with ear funnel, for example in the case of the first embodiment of the attachment 1 with ear funnel 18, an inner volume of the ear funnel 18 is subdivided into a supply air channel 20 and an exhaust air channel 21 by the guide vane base 25 and, optionally, the first guide vane cheek 26 and the second guide vane cheek 27. For this purpose, the longitudinal edges 16 of the guide vane base 25 or—if present—the adjoining guide vane cheeks 26, 27 may contact the ear funnel 18 directly either along their entire length or only in sections or may be slightly distanced from the ear funnel 18. In the case of contacting over the entire length of the guide vane 5, fluidic isolation between supply air channel 20 and exhaust air channel 21 can be achieved. In the case of only partial contacting or a spacing between guide vane 5 and ear funnel 18, complete insulation cannot be guaranteed, but it can be ensured that mixing of the air guided in the supply air channel 20 with the air guided in the exhaust air channel 21 is prevented as far as possible.

The supply air channel 20 connects the distal opening 29 of the connecting piece 4 to the outflow opening 22. The exhaust air channel 21 connects the inflow opening 23 of the ear funnel 18 with the outlet 24 of the attachment 1, which is formed as a recess in the housing of the ear funnel 18 on an underside of the latter. Accordingly, the supply air channel 20 allows the airflow produced by the device 2 to flow into the external ear canal 3 of the user and the exhaust air channel 21 allows the air used to dry the external ear canal 3 to flow back from the external ear canal 3 into the atmosphere.

In order to prevent the guide vane 5 from deforming during the intended use of the present teaching attachment 1 when the attachment 1 is inserted into the external ear canal 3, it may be provided that the ear funnel 18 is formed rigidly in comparison with the connecting piece 4 and/or the guide vane 5, preferably less flexible than the connecting piece 4 and/or the tongue 5. As a result of this measure, the ear funnel 18 protects in particular the guide vane 5 from possible deformation. For example, the ear funnel 18 may be made of polyethylene or polypropylene, while the connecting piece 4 and vane 5 may be made of thermoplastic elastomer or silicone.

Figure 5A:
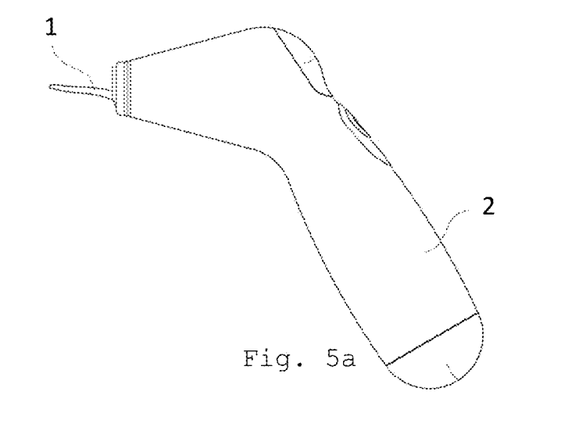
FIG. 5a shows an ear drying apparatus according to the present teaching, comprising the attachment according to the first embodiment without ear funnel.
Figure 5B:
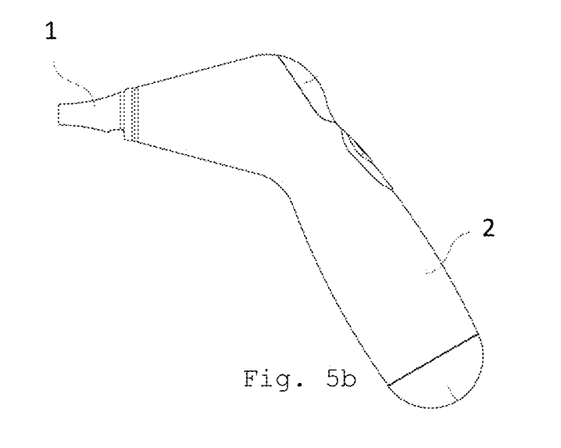
FIG. 5b shows an ear drying apparatus according to the present teaching, comprising the attachment according to the first embodiment with ear funnel.
Figure 5C:
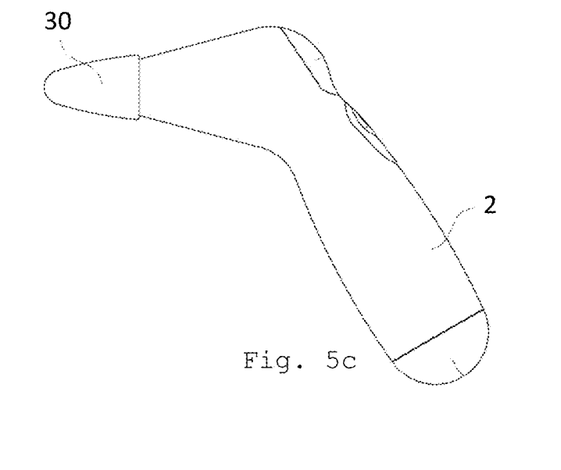
FIG. 5c shows the ear drying apparatus according to the present teaching with a protective cap.

FIG. 3a shows attachment 1 in a connection position in which attachment 1 is connected to device 2 for generating an airflow (see also FIGS. 5a, 5b and 5c).

For the purpose of connection, the attachment 1 with the connecting piece 4 is inserted in sections into the outlet opening 15 for the airflow of the device 2 for generating an airflow. A snap-in projection 17 at a device end section of the connecting piece 4 prevents an unintentional release of the connection between the device 2 for generating an airflow and the attachment 1. Basically, however, many different types of connection of the attachment 1 to the device 2 are conceivable. The airflow emerging from device 2 therefore first flows through the connecting piece 4 of attachment 1 when it flows into attachment 1. This is also the case if the connecting piece 4 is not inserted into the outlet opening 15 but is connected to the device 2 in some other way, for example by sliding it onto it.

A spacer 28 arranged, at least in sections, circumferentially around the circumference of the connecting piece 4 is positioned against a housing of the device 2 for generating an airflow and thus ensures that the connecting piece 4 cannot be pushed deeper than provided into the outlet opening 15. In the case of the embodiments of the attachment with ear funnel, e.g. in the case of the first embodiment with ear funnel 18 according to FIG. 3b, for example, the ear funnel 18 can be pushed onto the connecting piece 4 for the purpose of connection and be positioned against the spacer 28. Here, connecting piece 4 and ear funnel 18 are connected to each other by friction, wherein other connection options also exist—for example by means of interlocking latching grooves and latching projections.

FIG. 5a shows an ear drying apparatus in accordance with the present teaching, comprising the device 2 for generating an airflow and the attachment 1 in accordance with the present teaching and in accordance with the first embodiment of the attachment in accordance with the present teaching, wherein the ear funnel 18 has been removed from the integrally formed unit consisting of connecting piece 4 and guide vane 5 and is therefore not visible.

Device 2 is preferably specially designed for the purpose of drying ears and may preferably be formed so as to be portable.

FIG. 5b shows the ear drying apparatus according to the present teaching, comprising the device 2 for generating an airflow and the attachment 1 according to the present teaching with ear funnel 18.

FIG. 5c shows the ear drying apparatus according to the present teaching from FIG. 5a or 5b. The attachment 1 is covered by a protective cap 30, which serves in particular to protect the attachment 1 during the transport of the device 2.

Figure 6A:
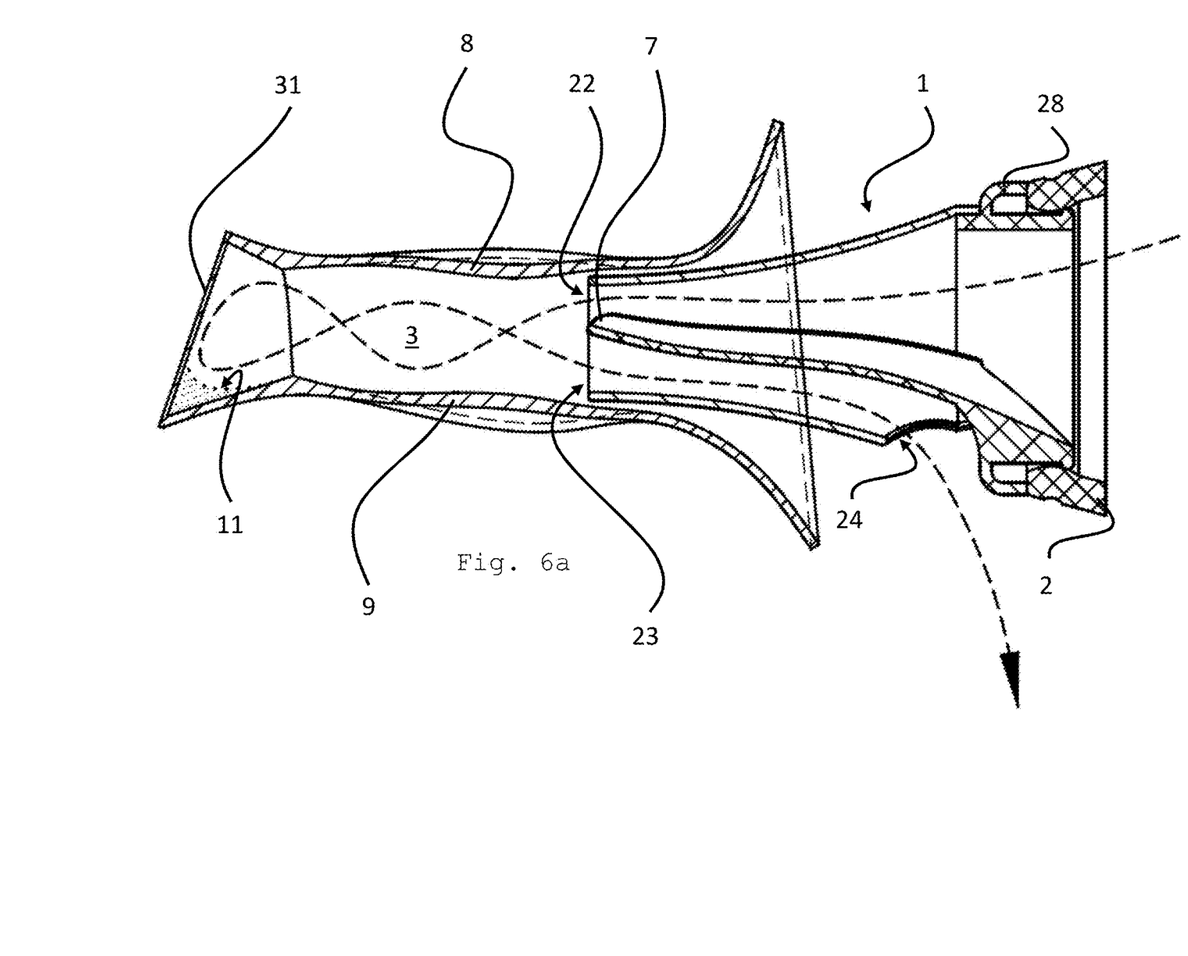
FIG. 6a shows a first flow course in an external ear canal, which was produced by the attachment according to the present teaching.

FIG. 6a is a schematic representation of the flow characteristic of a device according to the present teaching in its operating state, which is conditioned by attachment 1. The flow pattern depicted inside the external ear canal 3 is created in the same way, regardless of the concrete embodiment of the attachment 1 according to the present teaching. Due to the comparatively high insertion depth of attachment 1 into the external ear canal 3, there is no reflection of the airflow leaving attachment 1 at the side walls 8, 9; the airflow is swirled due to the guide vane 5 when leaving attachment 1, so that a vortex field favorable for drying is created inside the external ear canal 3.

Figure 6B:
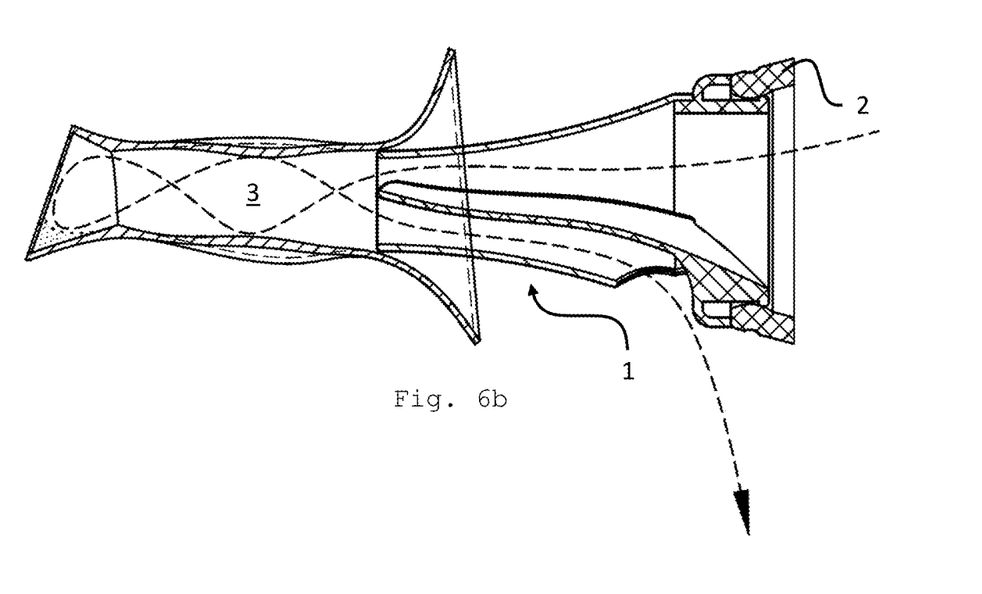
FIG. 6b shows a second flow course in an external ear canal, which was produced by the attachment according to the present teaching.

FIG. 6b also shows attachment 1 inserted into the ear canal 3, but with a smaller insertion depth than in FIG. 6a.

This results in a different flow pattern inside the external ear canal 3, which in turn is independent of the selected embodiment of attachment 1. In this case, the airflow exiting from attachment 1 is reflected on the side walls 8, 9 of the external ear canal 3, so that a vortex field favorable for drying is created inside the external ear canal 3.

Figure 6C:
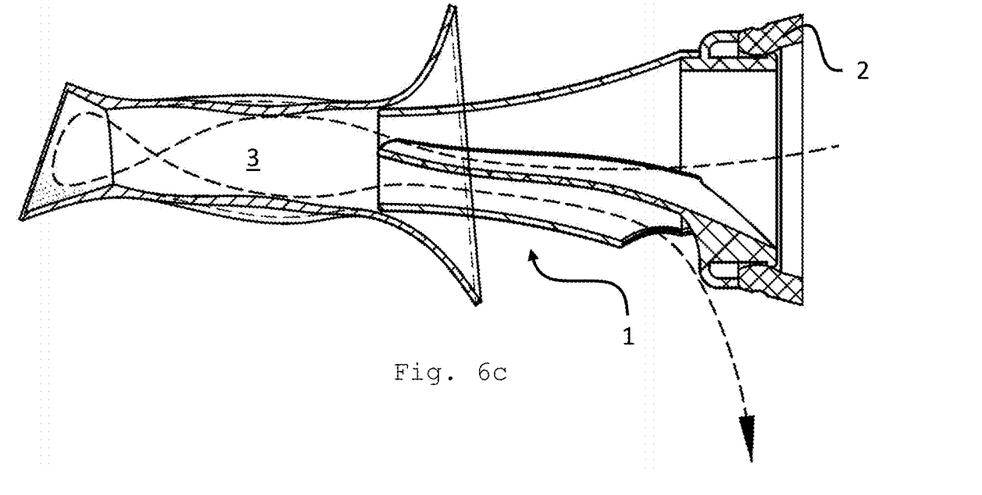
FIG. 6c shows a third flow course in an external ear canal, which was produced by the attachment according to the present teaching.
Figure 7A:
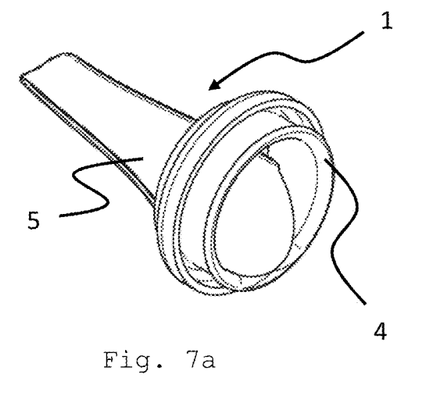
Figure 7B:
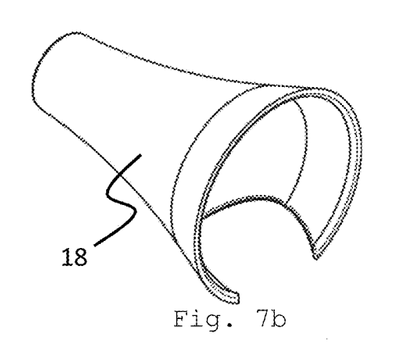
FIG. 7b shows a line representation of FIG. 1b.
Figure 7C:
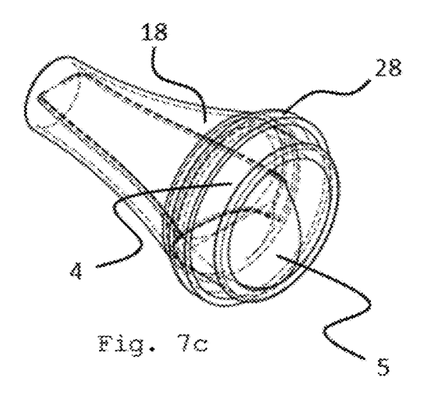
Figure 7D:
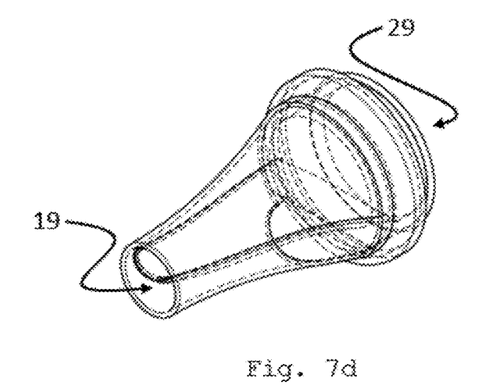
FIG. 7d shows a line representation of FIG. 2b.

FIG. 6c shows attachment 1 inserted into the ear canal 3, wherein the ear drying apparatus is operated however with different operating parameters, resulting in a different outlet angle of the airflow from attachment 1. This results in a different flow pattern inside the external ear canal 3, which in turn is independent of the selected embodiment of attachment 1. In this case too, the airflow leaving attachment 1 is reflected on the side walls 8, 9 of the external ear canal 3, so that a vortex field favorable for drying is created inside the external ear canal 3.

The FIGS. 7a, 7b, 7c and 7d are line representations of FIGS. 1a, 1b, 2a and 2b.

The invention claimed is:

1. An attachment for a device for generating an airflow, a warm airflow, or for dispensing a fluid, which attachment is adapted to be introduced into an ear canal of a human or of an animal, wherein the attachment comprises:
a connecting piece connecting to the device, and
a guide vane, projecting from the connecting piece, for guiding air or fluid flowing out of the device, the guide vane having a guide vane base,
wherein the guide vane is arranged upstream of the connecting piece, and a first section of the guide vane has a longitudinal cross-sectional profile curved in a first direction, and a second section of the guide vane has a longitudinal cross-sectional profile curved in a second direction, and the two curved sections extend in an curved manner opposite to one another,
wherein the attachment further includes an ear funnel enveloping the guide vane along the longitudinal length of the guide vane and has a proximal opening, the attachment is adapted to insert into the ear canal when used as intended, such that the proximal opening is adapted to be closest to the eardrum, the ear funnel adjoining the connecting piece and projecting therefrom.

2. The attachment according to claim 1, wherein the ear funnel and the guide vane are formed in one piece and can be connected as a unit to the connecting piece.

3. The attachment according to claim 1, wherein the connecting piece, the guide vane, and the ear funnel are integrally formed.

4. The attachment according to claim 1, wherein, when viewing a longitudinal cross-section of the attachment, the guide vane base intersects a longitudinal axis of the attachment.

5. The attachment according to claim 1, wherein, when viewing a longitudinal cross-section of the attachment, the guide vane base intersects a longitudinal axis of the ear funnel.

6. The attachment according to claim 5, wherein the longitudinal axis of the ear funnel coincides with the longitudinal axis of the attachment.

7. The attachment according to claim 1, wherein the guide vane has two guide vane cheeks projecting from the guide vane base, namely a first guide vane cheek and a second guide vane cheek, wherein the guide vane base and the first and second guide vane cheeks form a guide channel.

8. The attachment according to claim 7, wherein the first guide vane cheek projects from a first longitudinal edge of the guide vane base and the second guide vane cheek projects from a second longitudinal edge of the guide vane base opposite the first longitudinal edge.

9. The attachment according to claim 1, wherein the first section and the second section merge directly into one another.

10. The attachment according to claim 1, wherein the guide vane is arranged completely inside the ear funnel.

11. The attachment according to claim 1, wherein the ear funnel tapers from the connecting piece towards the proximal opening of the ear funnel.

12. The attachment according to claim 1, wherein a proximal end of the guide vane is adapted to be arranged closest to the eardrum when used as intended.

13. The attachment according to claim 12, wherein the proximal end of the guide vane is adapted to subdivide the proximal opening of the ear funnel into an outflow opening for air flowing out of the attachment into the ear canal and an inflow opening for air flowing from the ear canal into the attachment.

14. The attachment according to claim 1, wherein the guide vane is adapted to subdivide an inner volume of the ear funnel into a supply air channel for air flowing from the attachment into the ear canal and an exhaust air channel for air flowing from the ear canal into the attachment, wherein the supply air channel connects the connecting piece to the outflow opening and wherein the exhaust air channel connects the inflow opening to an outlet of the attachment.

15. The attachment according to claim 14, wherein a cross-section of the supply air channel decreases in the direction of flow.

16. The attachment according to claim 1, wherein an outlet of the attachment is formed by an opening in a housing wall of the ear funnel.

17. The attachment according to claim 1, wherein the connecting piece and the guide vane are formed in one piece and can be connected as a unit to the ear funnel.

18. The attachment according to claim 1, wherein the connecting piece is formed by an end section of the ear funnel.

19. An ear drying apparatus, comprising a device for generating an airflow and an attachment according to claim 1.

* * * * *